United States Patent [19]

Tezel

[11] Patent Number: 4,476,864
[45] Date of Patent: Oct. 16, 1984

[54] COMBINED MULTIPLE PUNCH AND SINGLE PUNCH HAIR TRANSPLANT CUTTING DEVICE

[76] Inventor: Jirayr Tezel, 221 Falmouth Rd., Scarsdale, N.Y. 10583

[21] Appl. No.: 428,139

[22] Filed: Sep. 29, 1982

[51] Int. Cl.³ .............................................. A61B 17/32
[52] U.S. Cl. .................... 128/305.1; 128/305; 128/754; 128/755
[58] Field of Search ............... 128/305, 755, 753, 754, 128/355, 310, 305.1; 401/31, 35, 53, 37, 39, 43, 44; 30/301, 316

[56] References Cited

U.S. PATENT DOCUMENTS 3,867,942 2/1975 Bellantoni et al. .................. 128/305
3,979,819 9/1976 Nomura et al. .................. 408/35 X

FOREIGN PATENT DOCUMENTS 673273 7/1979 U.S.S.R. .............................. 128/305

Primary Examiner—Michael H. Thaler
Attorney, Agent, or Firm—Sherman & Shalloway

[57] ABSTRACT

A light weight, portable, hand held power actuated hair transplant plug cutting device is capable of making either simultaneous multiple punches or a single punch in the scalp of a patient. A single shaft member with removable cutting tip extends through one wall of the housing unit of the device, while a plurality of shaft members with removable cutting tips extends through the opposite wall of the housing unit. Actuation of the power drive causes rotation of both the single shaft member and the plurality of shaft members so that only the single cutting device is needed to make all of the punches required for the hair transplant operation. Tools are provided for placing and removing disposable cutting tips on and from the shaft members.

5 Claims, 10 Drawing Figures

COMBINED MULTIPLE PUNCH AND SINGLE PUNCH HAIR TRANSPLANT CUTTING DEVICE

BACKGROUND OF THE INVENTION

1. Field of the Invention

This invention relates to a power operated device for cutting plugs in the scalp of a patient undergoing a hair transplant operation which combines multiple punch cutting tips with a single punch cutting tip, in which all of the tips are removable. More particularly, this invention relates to a portable, power operated unit combining the capability to make multiple plug cuts in broad areas of the scalp and single plug cuts in narrower areas of the scalp to facilitate hair transplant operations, incorporating removable tips to facilitate replacement.

2. Discussion of the Prior Art

Manual single punch cutting tools and power driven single punch cutting tools for hair transplant operations are known. The latter are described, for example, in two literature articles "Miniature Drill Expedites Hair Transplantation", Jirayr Tezel, M.D., CUTIS, Cutaneous Medicine for the Practioner, Vol. 6, No. 4, pp. 461-462 (April 1970); and "Adjunct in Hair Transplantation: The Power Activated Punch", Jirayr Tezel, M.D., Dermatology Digest, Vol. 6, pp. 21-34 (April 1967). A manual single punch with removable cutting head is described in U.S. Pat. No. 4,122,855—(Tezel) See also U.S Pat. No. 4,210,145—(Nestor and Devine), Surgical Hole Cutter for Square Hole Transplant Plugs.

A multiple punch power driven unit is known from U.S Des. Pat. No. 220,987, Frank A. Ballentoni. Power driven punches have several advantages, for example, generally many more incisions can be made in a given period, thereby reducing the patient sitting time for a given number of plugs. The incisions can often be made with less discomfort to the patient and also with less fatigue to the doctor. Naturally, power driven multiple punch devices display these advantages more so than single punch power driven cutting devices.

Nevertheless, for many areas of the patient's scalp or to fill in spaces where a greater density of plugs may be required or desired for cosmetic reasons, it is often necessary to make only a single incision at a time. Rather than changing equipment for changing from multiple to single or from single to multiple incisions it would be highly desireable and advantageous to be able to use a single power driven device capable of easily shifting from a single punch capability to a multiple punch capability. However, no device meeting this objective is known to the inventor.

SUMMARY OF THE INVENTION

The drawbacks of the prior art devices are eliminated by the combined multiple punch/single punch hand manipulatable power actuated cutting device according to the invention. The hair transplant plug cutting device of this invention includes a portable hand held power source having a drive axle extending into a housing unit for simultaneously driving in rotation a plurality of shaft members extending out of the housing through a plurality of apertures in one wall thereof and a single shaft member extending out of the housing through a single aperture in an opposite wall thereof. Each of the shaft members has a cutting head attached to its free end so that it is possible to make either multiple punches using the plurality of cutting heads rotating on one side of the housing unit or a single punch using the single rotating cutting head on the opposite side of the housing unit. The rotation of the shaft members and associated cutting heads is accomplished by first drive means for rotatingly driving the single shaft member, second drive means for rotatingly driving each of the shaft members in the plurality of shaft members, and means for transmitting the driving power from the first drive means to the second drive means. The first drive means is driven by the drive axle of the power source to cause rotation of the single shaft member and simultaneous rotation of the plurality of shaft members via the power transmitting means and the second drive means.

In a specific embodiment, the first driving means includes a pair of engaged bevel gears, the first connected to the drive axle of the power source and the second connected to the single shaft member. The power transmitting means is connected to the single shaft member and rotates therewith and transmits the force of rotation to the second drive means. To this end the power transmitting means preferably includes a first spur gear mounted on the single shaft member and an idler gear engagingly connected thereto and to the second drive means which includes at least one gear train formed from a plurality of spur gears which are connected to and cause rotation of the plurality of shaft members.

Preferably, two gear trains are provided for rotating the plurality of shaft members, the first gear train being driven by the power transmitting means and being formed from a plurality of spur gears which is less in number than the plurality of shaft members. The second gear train is driven off one of the shaft members driven by the first gear train and is formed from a second plurality of spur gears which is also less in number than the plurality of shaft members, such that all of the shaft members are rotatingly driven by either the first or second gear trains.

Good results have been obtained using six shaft members arranged in two parallel, staggered rows with three shaft members in each row, with the shaft members in each row being uniformly spaced and slightly offset to accomodate the spur gears of the first and second drive trains. In this arrangement, rotation of all of the shaft members is accomplished by providing a spur gear on the middle shaft member of each of the rows and an additional spur gear on an outside shaft member of each row, each of the outside spur gears being driven by the respective middle spur gear in the same row. Preferably the outside spur gears are located on remote opposite outside shaft members, and the middle spur gear of one row is driven by the idler gear of the power transmitting means, and in turn, drives the middle spur gear of the second row. The four spur gears of the first drive train cause rotation of those four of the six shaft members to which they are attached. Rotation of the remaining two shaft members is provided by the second drive train with the driving power being taken off of the middle shaft member driven by the idler gear. To this end, a spur gear is provided on this driven middle shaft member and this spur gear in turn engages spur gears associated with each of the remaining two outside shaft members which are not driven by the first gear train. Naturally, a similar arrangement can be provided for any number of shaft members arranged in a single or multiple rows.

In order to obtain maximum stability, the gears of the power transmitting means and the second driven means, as well as the bevel gear connected to the single shaft member are supported by the walls of the housing unit, either directly, or through spacers or collars having a smooth bearing surface on which the gears may rotate with minimum friction and heat generation.

The patented disposable cutting heads are removably fixed to the shaft members so that they may be disposed of after use. However, if desired, the used cutting heads may be sterilized or sharpened, as necessary, and re-used. Special pushing and pulling tools are provided for inserting and removing the cutting heads from the shaft members.

The portable hand held power source can be any light weight motor unit and can be controlled by a foot pedal rheostat control unit or by suitable hand operated switches on the motor housing. A foot pedal control is advantageous in that the surgeon can have better manual control of the cutting device and cutting area.

Naturally, means other than gear systems for driving the shaft members can readily be envisioned, for example, friction belts, chains, and the like. It is also possible, and within the scope of the invention to provide a clutch or other similar means for disengaging the power transmitting means from the second drive means for the multiple grouped cutting heads when the single shaft member and associated cutting head are being used. It is also within the scope of the invention to drive the second drive means directly off the drive axle of the motor and drive the first drive means for the single shaft off of the second drive means.

Many other alternatives and variations will be apparent to the artisan and these should also be considered to be within the scope of the invention which will be defined hereinafter by the appended claims and any obvious variants or equivalents thereof.

The invention will now be described in greater detail in connection with a specific embodiment thereof and with the aid of the accompanying drawings in which:

FIG. 6 is a view of a cutting head for use in the present invention;

FIG. 7 and FIG. 8 are perspective views of a pushing and pulling tool, respectively, for inserting and removing a cutting head on or from a shaft member.

Figure 1:
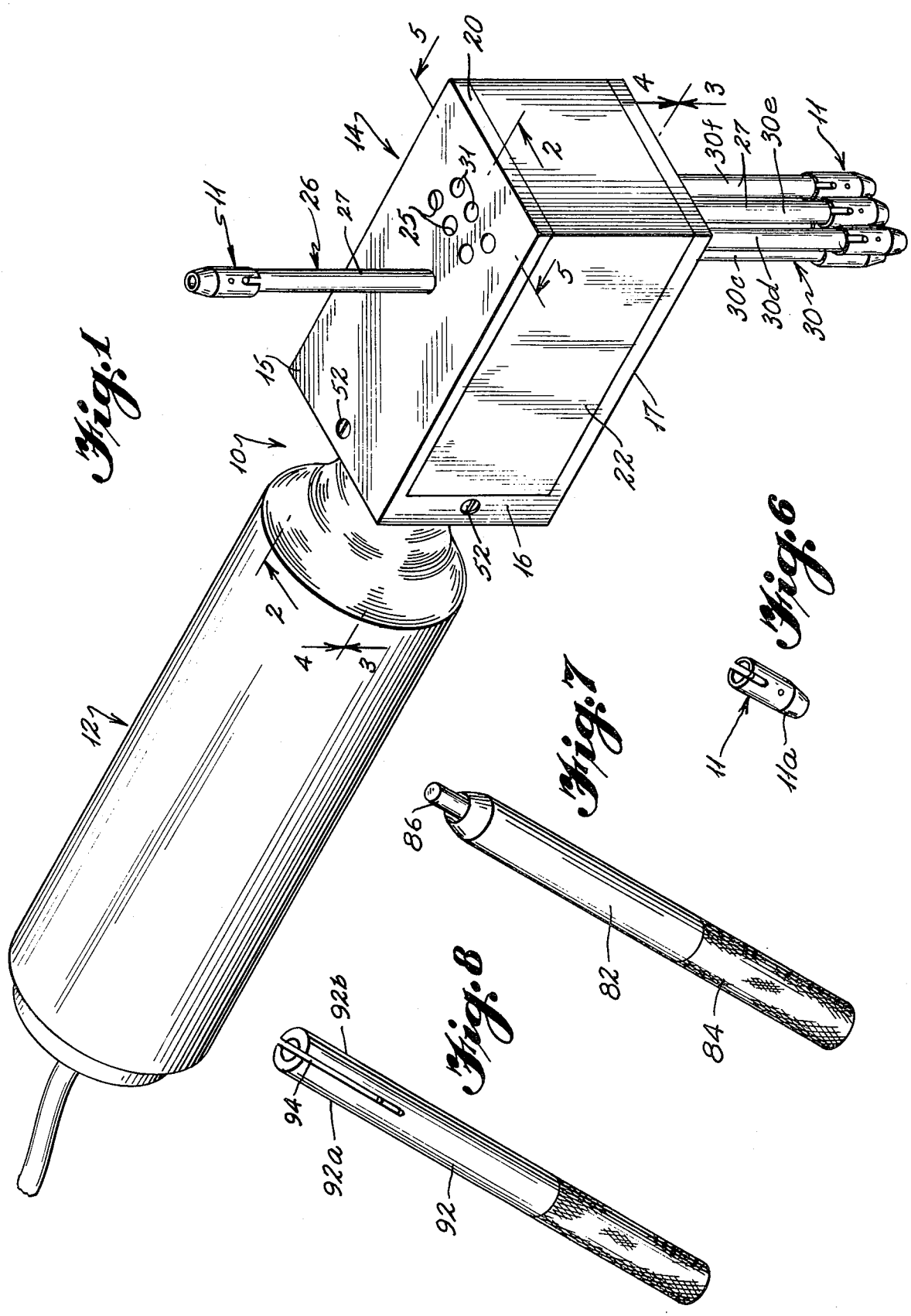
FIG. 1 is a perspective view of an embodiment of the hair transplant cutting device according to the invention.
Figure 2:
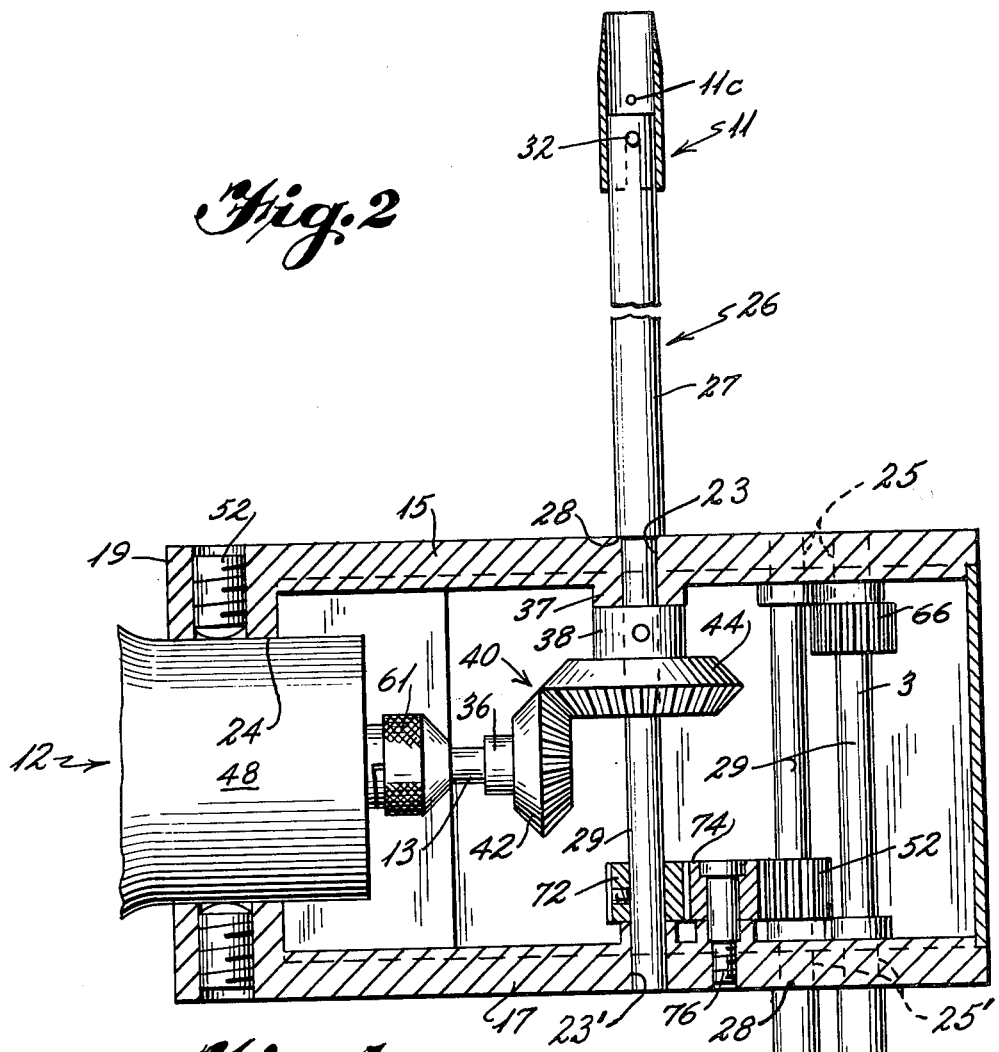
FIG. 2 is a partial sectional view, in elevation, taken along line 2—2 of FIG. 1.
Figure 5:
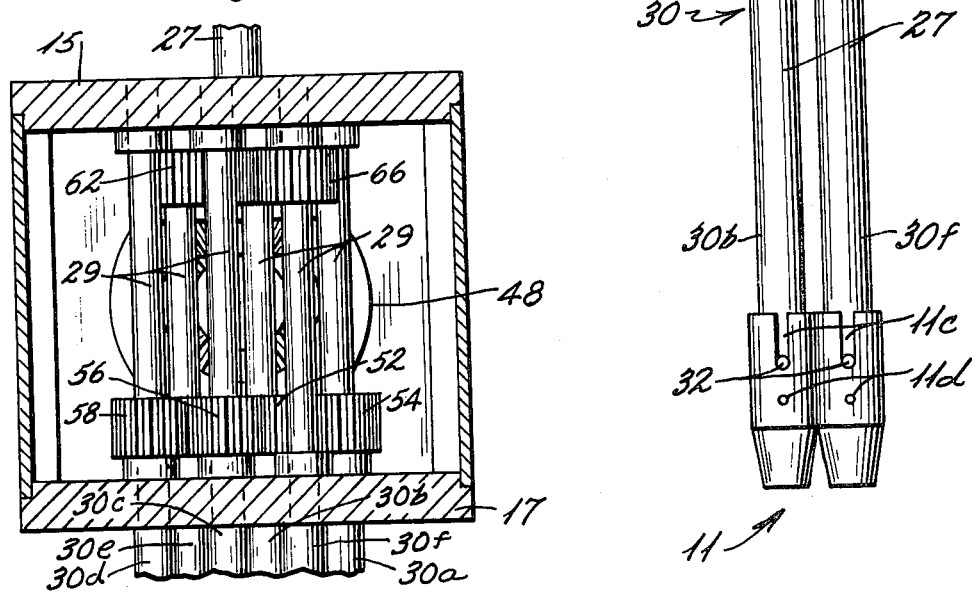
FIG. 5 is a sectional end view, in elevation, taken along line 5—5 of FIG. 1.

As seen in FIG. 1, the cutting device 10 is powered by a portable hand held electrically powered motor 12, such as a Dremel Moto-Tool Model No. 260, a product of Dremel Manufacturing Co., Racine, Wis. This is an 0.5 ampere motor which can be operated from a conventional 110 volt electric outlet and is capable of producing as much as 30,000 rpm. A foot-controlled rheostat (not shown) starts the motor and controls the speed. The neck 48 of the motor fits within the housing unit 14 made from light weight metal through the opening 24 in end wall 19 and is secured in place by four set screws, one in each side wall 15, 16, 17 and 18 of the housing unit. A removable U-shaped cover 22 extends over side walls 16 and 18 and end wall 20 to provide access to the mechanical works inside the housing unit.

A single shaft member 26 extends out of the housing unit through an aperture 23 in one side wall 15 while a plurality (six) of shaft members 30 arranged in two slightly staggered rows of three shaft members each extend out of the housing unit through a corresponding plurality of apertures 25' in the opposite side wall 17. Cutting heads 11 (see FIG. 6) are removably but securely fitted over the free ends of the shaft members. Both the cutting heads and shaft members can conveniently be fabricated from stainless steel, the latter being of solid metal.

Each of the shaft members 26 and 30 has a main body portion 27 and coaxial therewith a spindle-like extension 29 having a reduced diameter relative to the main body portion thereby forming a shoulder 28 at the interface between the two portions. Main body portion 27 extends outside of the housing such that shoulder 28 abuts against side wall 15 in the case of shaft member 26 or side wall 17 in the case of shaft members 30. The length of main body portion 27 is not particularly critical but will generally be from about 1 to about 2 inches. The diameter of the main body portion is also not particularly critical as long as sufficient mechanical strength and rigidity is provided. Generally, a diameter of from about 0.1 to about 0.15 inches is sufficient.

The diameter of the spindle-like extension 29 is also not particularly critical but will generally be from 0.005 to 0.02 inch less than the diameter of the main body portion such that the annular shoulder 28 has a width of from about 0.0025 to about 0.01 inch. The length of spindle 29 is preferably the same as the distance between the outside surfaces of walls 15 and 17 so that the spindle is firmly, but rotatingly, embedded in the holes 23, 23', extending through side walls 15 and 17, respectively, for shaft member 26 or in the holes 25, 25' similarly extending through side walls 15 and 17, respectively, for shaft members 30. However, the length of the spindle 29 can be shorter than this distance so long as the free end 31 of the spindle extends at least partially into one of the bores 23 or 25' as the case may be. The bores 23, 23', 25 and 25' may be provided with bearing surfaces, e.g. brass cylinders having the same nominal diameter as that of the spindle portion so that the spindles, and therefore, the entire shaft member may freely rotate when driven.

Although the actual dimensions of the housing unit are not critical, in actual practice good results have been obtained with an aluminum metal housing measuring about 1½ inches on each side and about 2¾ inches in length. A ⅜ inch diameter opening 24 in end wall 19 can easily but securely accommodate the neck of the Dremel Moto-Tool. The combination of the miniature motor and aluminum housing make the device sufficiently compact and lightweight to be easily manipulated by the surgeon without inducing fatigue or muscle strain during extended usage.

Specific dimensions for the stainless steel shaft members which have been used include an overall length of 2¾ inches and a diameter of 0.135 inch × 1¼ inches long for the main body portion 27 while the spindle like extension measures ⅛ inch diameter × 1½ inches long. The spindle-like extensions are fitted in the side walls through 3/16 inch diameter holes which are press fitted with ⅛ inch I.D. by 3/16 inch long bronze bearings.

In the preferred arrangement of the cutting device the single aperture for the individual shaft member will be located on the one side wall closer to the end wall through which the motor is connected then to the opposite end wall and will be located on the longitudinal center line of the one side wall, while the plurality of apertures in the opposite side wall will be arranged in at least two parallel rows with at least two apertures in each row, preferably two rows of three apertures each, with the centers of the apertures in one row slightly offset from the centers of the appertures in the adjacent row, and the plurality of apertures will be approximately centered with respect to the longitudinal centerline of the opposite side wall and will be closer to the opposite end wall than to the end wall through which the motor passes.

The connection between the motor and the mechanical works for driving the shaft members and cutting heads is shown in FIGS. 2–5.

The first means for driving the shaft member 26 is shown generally at 40 and includes a first bevel gear 42 connected to the drive axle 13 of motor 12 through collar 36 and second bevel gear 44 which is fixed to the spindle by collar 38 which also is fitted over the spindle and abuts boss 37 on the inside surface of wall 15.

Figure 3:
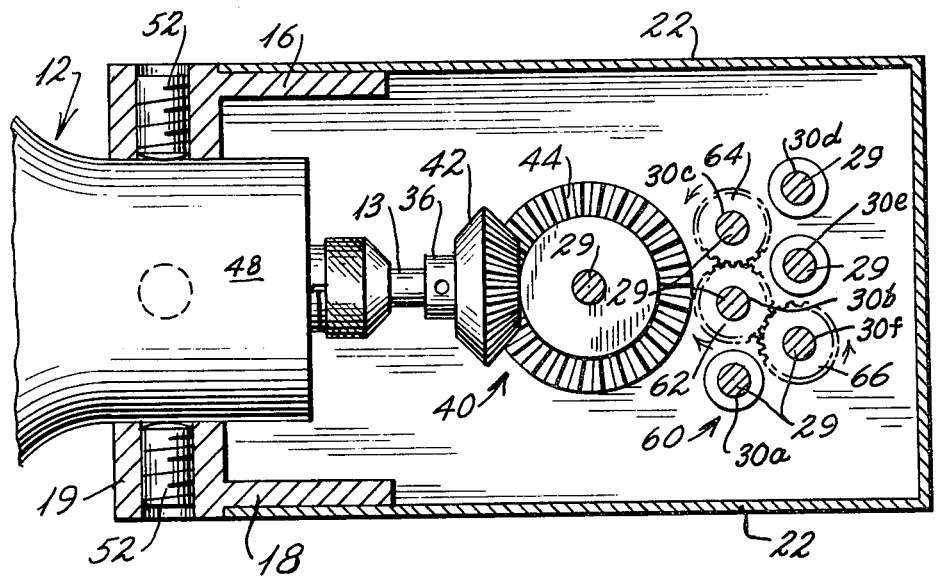
FIG. 3 is a partial sectional view, in the direction of line 3—3 of FIG. 1.

The second drive means for rotating the shaft members 30 includes a first drive train indicated at 50 (FIG. 4), adjacent to the lower side wall 17 and a second drive train adjacent to the upper side wall 15 and indicated generally at 60 (FIG. 3).

The power transmitting means for transferring the driving power from the first drive means 40 to the second drive means—which in the preferred illustrated embodiment includes drive trains 50 and 60—is shown generally at 70 (FIG. 4) and includes a first spur gear 72 fixedly mounted to the spindle of shaft member 26 and idler gear 74 driven by spur gear 72. Gears 72 and 74 are also adjacent to side wall 17 and abut against bosses on the inside surface of side wall 17. Idler gear 74 is rotatingly secured to the housing by threaded screw 76.

Figure 4:
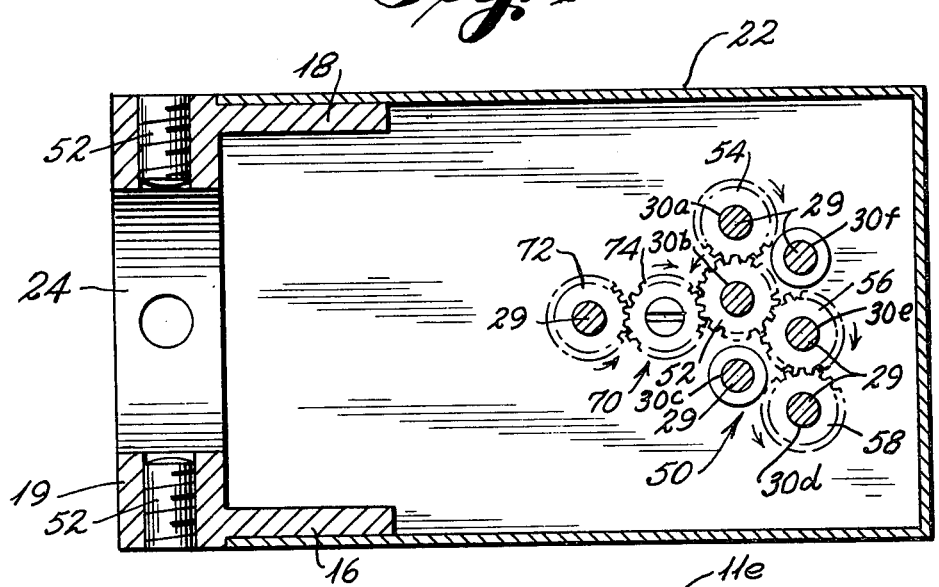
FIG. 4 is a sectional view, taken along line 4—4 of FIG. 1.

As best seen in FIG. 4 drive train 50 includes a second spur gear 52 mounted on the spindle of middle shaft 30b of the first row of shaft members 30, a third spur gear 54 mounted to the outside shaft member 30a of the first row, a fourth spur gear 56 mounted to the middle shaft member 30e of the second row of shaft members, and a fifth spur gear 58 which is mounted to shaft member 30d which is the outer member of the second row which is most remote from outer member 30a of the first row. Spur gear 52 is engaged with and driven by idler gear 74. Spur gears 54 and 56 are each engaged with and driven by spur gear 52 while spur gear 58 is engaged with and driven by spur gear 56. Accordingly, the first drive train 50 through spur gears 52, 54, 56 and 58 causes rotation of shaft members 30b, 30a, 30e and 30d, respectively.

The remaining shaft members 30c and 30f are respectively driven by spur gears 64 and 66 which together with spur gear 62, which is mounted and rotates with the spindle of shaft member 30b, form the second drive train 60 (FIG. 3). Accordingly, when motor 12 is actuated, all of the shaft members are simultaneously rotated so that the surgeon may make either a single incision using the cutting head attached to shaft member 26 or a plurality of incisions using the cutting heads attached to shaft members 30, simply by rotating housing 14 by 180°. Actually, in practice, it is only necessary to turn the handle of motor 12 to obtain the proper orientation and alignment of the cutting heads For the previously given dimensions for the housing and shaft members, using the Dremel Motor-Tool Model 260, proper fit and range of rotation speeds are provided with miter and bevel gears 42 and 44 having a ratio of 1 to 2 and 96 pitch, and spur gears at 120 pitch and 3/32 inch face. All of the gears have ⅛ inch bores and may be secured to their respective shaft members with set screws.

It will be appreciated that each of the shaft members 30 will be rotated at the same speed of rotation but not necessarily in the same direction. With the arrangement illustrated for the preferred embodiment shaft members 30a, 30c, 30e and 30f will rotate in one direction (as shown by the arrows in FIGS. 3 and 4) while shaft members 30b and 30d will rotate in the opposite direction (see the arrows in FIGS. 3 and 4).

In operation, the appropriate number of sterile cutting heads (7 in the illustrated embodiment) are fitted to the free ends of the main body portions 27 of shaft members 26 and 30. This is easily accomplished using the pushing or mounting tool 82 (FIGS. 7 and 9) in the form of a solid metal rod having a cutting head gripping device at one end thereof.

The cutting heads may be formed from hollow stainless steel tubing having one tapered end 11a ground to a circular cutting edge 11b. The opposite end has two longitudinal slots 11c circumferentially spaced about 180° apart and extending about one-fourth of the length of the cutting head. Two air escape holes 11d are also provided on opposite sides of the cutting head to permit fluid, e.g. blood, drainage, as described for example in U.S. Pat. No. 4,122,855.

Figure 9:
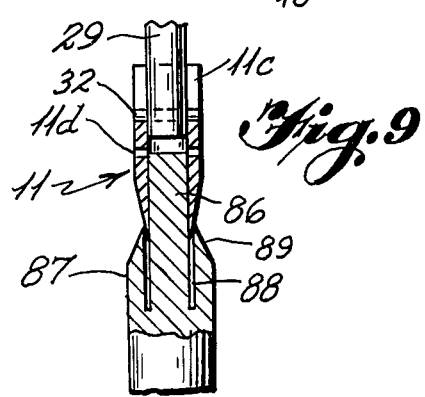
FIG. 9 and FIG. 10 are partial sectional view illustrating the manner of using the pushing and pulling tools of FIGS. 7 and 8, respectively, in inserting or removing a cutting head, on or from a shaft member.

To fit the cutting head on the shaft member without damaging the cutting edge, the gripping device of pushing tool 82 includes a cylindrical pin 86 having substantially the same diameter as the insider diameter of the cutting head, which in turn is about the same as the diameter of main body portion 27, for example, about 0.135 inch. Pin 86 extends from within a recess at the end of the metal rod and is surrounded by shoulder 87 having a tapered truncated conical end 89. A narrow annular space 88 is formed between pin 86 and shoulder 87. The tapered end and cutting edge of the cutting head fit within the annular space 88 and is securely gripped above the cutting edge by the conical end 89 when pin 86 is inserted into the cutting head as shown in FIG. 9. The cutting head can then be force fitted over the free end of the shaft member until the edges of slots 11c reach pin 32 provided near the free end and extending slightly from opposite sides of the shaft member. The air holes 11d are located sufficiently far from the edges of slots 11c to be clear of the shaft member when the cutting head is in place, i.e. when the edges of slots 11c are stopped by pin 32.

The actual cutting operation is substantially the same as for other manual or power actuated punches.

Either before or after the sterile cutting heads are put in place, a bald area of the head into which hair is to be grated, and an area of the head from which hair follicles are to be taken, are both anesthetized by injection of a local anesthetic. Cutting device 10 is then used to cut out multiple or single plugs in the bald portion of the scalp thereby leaving sockets. Then, using the single cutting head on shaft member 26, the cutting device is used to cut or bore out individual hair-bearing plugs from the portion of the scalp bearing hair. The hair-bearing plugs are removed from the scalp with blood on the side periphery of the plugs being drained through holes 11d. Once each hair-bearing plug is removed, the hair thereon may, if necessary, be trimmed to proper length. The prepared hair-bearing plugs are then placed in the punched-out sockets where they are held in place by the remaining blood in the sockets which congeals after a short period of time. After bleeding has ceased, the scalp is appropriately dressed and bandaged.

Figure 10:
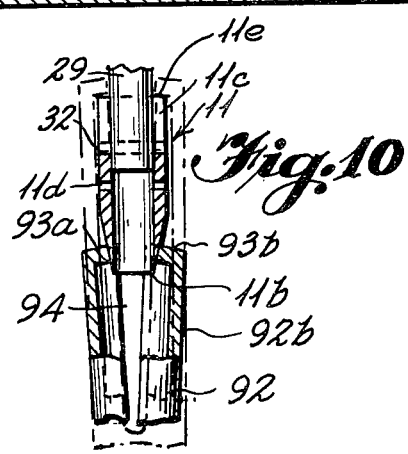

After all the punches have been made, the cutting heads can be removed using pulling tool 92 which is a hollow metal rod provided at one end with two elongated longitudinal slots 94 on opposite sides thereof. The two halves of the rod 92a, 92b, on either side of slots 94 each terminate with inwardly projecting ribs 93a, 93b, respectively. When the slotted end of tool 92 is forced over the tapered end 11a (as shown in FIG. 10), the ribs 93a, 93b slidingly engage the tapered end causing the halves 92a, 92b to spread apart. Further pushing of tool 92 until ribs 93a, 93b slide over the non-cutting end 11e permits halves 92a, 92b to spring back together to the normal position with ribs 93a, 93b engaging end 11e. Tool 92 is then tightly gripped thereby enabling the cutting head to be pulled off of the shaft member without contacting or damaging the cutting edge simply by withdrawing the pulling tool 92 from the shaft member.

It can, therefore, be appreciated that this invention allows the hair transplant surgeon to conveniently make both single punches or multiple punches for making single sockets or multiple sockets and single hair bearing plugs from a patient undergoing a hair transplant operation, without requiring the surgeon to change tools. The device is lightweight and compact and, therefore, easily manipulated without causing fatigue or strain so that more sockets and hair-bearing plugs can be taken in a single sitting, while minimizing the discomfort to the patient.

What I claim is:

1. A power driven multiple punch cutting device for making either single or multiple punches in the scalp of a patient undergoing a hair transplant operation, comprising a housing having a plurality of apertures in a first wall thereof and a single aperture in a second wall thereof opposite to said first wall;

a plurality of shaft members extending through said housing from said second wall to said first wall and perpendicularly outward from said first wall through said plurality of apertures;

a single shaft member extending through said housing from said first wall to said second wall and perpendicularly outward from said second wall through said single aperture;

first means for rotatingly driving said single shaft member comprising a first bevel gear connected to said power source and a second bevel gear connected to said single shaft member and driven by said first bevel gear;

second means for rotatingly driving each of said plurality of shaft members comprising a first gear train adjacent said first wall and a second gear train adjacent said second wall wherein said first and second gear trains comprise a plurality of spur gears, one of which spur gears in said first gear train is driven by an idler gear and causes rotation of the remainder of the plurality of spur gears which in turn rotatingly drive said plurality of shaft members;

means for transmitting the driving power from said first drive means to said second drive means comprising a first spur gear connected to said single shaft member spaced from said second bevel member and adjacent said first wall, and said idler gear adjacent said first wall and driven by said first spur gear;

a power source for driving said first drive means, whereby driving of said first drive means by said power source causes rotation of said single shaft member and simultaneous rotation of said plurality of shaft members through said power transmitting means and said second drive means, respectively; and cutting heads attached to the free ends of each of said single shaft member and said plurality of shaft members;

whereby said device is capable of making either simultaneous multiple punches through the cutting heads attached to the plurality of rotating shaft members or a single punch through the cutting head attached to the single rotating shaft member.

2. The hair transplant cutting device of claim 1 wherein the plurality of shaft members comprises six shaft members arranged in a first row with three shaft members and a second row with three shaft members said first row being parallel to said second row, the axes of the shaft members in each row being equidistant from each other and offset from the axes of the shaft members in the other row.

3. The hair transplant cutting device of claim 2 wherein said first drive train comprising a second spur gear connected to the middle shaft member of said first row and driven by said idler gear, a third spur gear connected to an outside shaft member of said first row and driven by said second spur gear, a fourth spur gear connected to the middle shaft member of said second row and driven by said second spur gear, and a fifth spur gear connected to an outside shaft member of said second row which is most remote from said outside member of the first row to which said third spur gear is connected, said fifth spur gear being driven by said fourth spur gear, said second drive train comprising a sixth spur gear connected to the middle shaft member of said first row, a seventh spur gear connected to the other outside shaft member of the first row and driven by said sixth spur gear and an eighth spur gear connected to the other outside shaft member in the second row and driven by said sixth spur gear.

4. The hair transplant cutting device according to claim 1 wherein the cutting heads are detachably connected to said shaft members.

5. The hair transplant cutting device according to claim 1 wherein said power source is a portable hand held electrically powered motor having a drive axle for driving said first drive means.

* * * * *